(12) United States Patent
Watts

(10) Patent No.: US 9,488,612 B2
(45) Date of Patent: Nov. 8, 2016

(54) LUBRICANT TEST METHOD

(71) Applicant: Infineum International Limited, Abingdon (GB)

(72) Inventor: Raymond F. Watts, Long Valley, NJ (US)

(73) Assignee: Infineum International Limited, Abingdon, Oxfordshire (GB)

( * ) Notice: Subject to any disclaimer, the term of this patent is extended or adjusted under 35 U.S.C. 154(b) by 237 days.

(21) Appl. No.: 14/295,530

(22) Filed: Jun. 4, 2014

(65) Prior Publication Data

US 2015/0355122 A1     Dec. 10, 2015

(51) Int. Cl.
*G01N 27/06*     (2006.01)
*G01N 33/26*     (2006.01)

(52) U.S. Cl.
CPC .............. *G01N 27/06* (2013.01); *G01N 33/26* (2013.01)

(58) Field of Classification Search
CPC .............................. G01N 33/26; G01N 27/06
USPC .......................................................... 73/1.02
See application file for complete search history.

(56) References Cited

U.S. PATENT DOCUMENTS

| | | | | |
|---|---|---|---|---|
| 4,686,857 A | * | 8/1987 | Kato ................... | G01N 33/2888 324/698 |
| 2005/0145706 A1 | * | 7/2005 | Cardinali Ieda .... | F16H 57/0413 236/93 R |
| 2006/0257275 A1 | * | 11/2006 | Park ...................... | F04B 35/045 417/417 |
| 2010/0180663 A1 | * | 7/2010 | Sun ...................... | G01F 23/265 73/1.02 |
| 2012/0229152 A1 | * | 9/2012 | Katafuchi .......... | G01N 33/2876 324/672 |

* cited by examiner

*Primary Examiner* — Jeff Natalini
(74) *Attorney, Agent, or Firm* — Andrews Kurth Kenyon LLP

(57) ABSTRACT

A method of determining the compatibility of a lubricating fluid with an energized electrical or electronic component comprises:
(a) contacting a test apparatus with the fluid;
(b) applying an electrical current to the test apparatus; and
(c) monitoring the current flow through the test apparatus over time.

The test apparatus includes at least one pair of conductors separated by an insulator that does not extend across the whole of the opposing surfaces of the conductors. The electrical current is applied across the pair of conductors. Also described is a device for performing the method, a method of selecting a lubricant and a lubricant so selected.

11 Claims, 2 Drawing Sheets

LUBRICANT TEST METHOD

This invention relates to a method of determining the compatibility of lubricating fluids with energized electrical or electronic components when such fluids are placed in contact with them, and to a device for performing the method.

BACKGROUND OF THE INVENTION

Many modern pieces of mechanical equipment are controlled by, or incorporate, electrical or electronic devices. Such pieces of equipment often contain fluids which may be used for lubrication, power transmission or cooling. In the context of this application, a lubricating fluid should be construed broadly to include fluids which perform functions other than pure lubrication, e.g. cooling etc. For reasons of saving space and weight, it is often desirable to locate the electrical or electronic devices in areas of the equipment where they are in direct contact with a fluid and it is not always possible or desirable to completely isolate the devices from the fluid. Situations therefore arise where an electrical or electronic device is energized whilst in contact with a fluid. This can give rise to chemical reactions which may damage the device, degrade the fluid, or both. For example, the fluid may begin to corrode the metallic conductors of a device or the degradation of the fluid may permit the conduction of electricity across normally unconnected parts of the device. Ultimately, failure of the device may occur through severe corrosion or short-circuit.

Examples of electrical devices susceptible to this type of damage include those found in vehicle transmissions, either manual or automatic; engines; pumps and the like which contain fluids such as transmission oils, automatic transmission fluids (ATF) continuously variable transmission fluids (CVTF), a dual clutch transmission fluids (DCTF), engine oils, axle and differential oils, and hydraulic fluids.

The electrical and electronic devices found in modern mechanical equipment are often complex so the evaluation of these devices in-situ using real equipment can be costly and time consuming. Therefore, there exists a need to be able to evaluate the fluids' compatibility with these devices, which ultimately enables one to be able to predict equipment life. Several tests exist for the determination of the compatibility of lubricating oils with metals, e.g., the ASTM D-130-12 Standard Test Method for Corrosiveness to Copper from Petroleum Products by Copper Strip Test and the ASTM D-665-12 Standard Test Method for Rust Preventing Characteristics of Inhibited Mineral Oil in the Presence of Water. Both of these methods assess compatibility of lubricants with metals via simple exposure. No simple test currently exists to evaluate the impact of lubricants and other non-conducting fluids on energized electrical circuits in contact with such fluids. The present invention provides such a test and a device suitable for performing it.

SUMMARY OF THE INVENTION

Accordingly in a first aspect, the present invention provides a method of determining the compatibility of a lubricating fluid with an energized electrical or electronic component, the method comprising:
(a) contacting a test apparatus with the fluid;
(b) applying an electrical current to the test apparatus; and
(c) monitoring the current flow through the test apparatus over time;

wherein the test apparatus comprises at least one pair of conductors separated by an insulator; wherein the insulator does not extend across the whole of the opposing surfaces of the conductors; and wherein the electrical current is applied across the pair of conductors.

In a second aspect, the present invention provides a device for determining the compatibility of a lubricating fluid with an energized electrical or electronic component, the device comprising a fluid reservoir and a test apparatus having at least one pair of conductors separated by an insulator, wherein the insulator does not extend across the whole of the opposing surfaces of the conductors; a current source adapted to apply an electrical current across the or each pair of conductors; monitoring means to monitor the current flow through the test apparatus over time; wherein the test apparatus is configured such that in use, the conductors are in contact with the fluid.

In a third aspect, the present invention provides a method of selecting a lubricant, the method comprising testing candidate lubricants using a device according to the second aspect and selecting from the candidate lubricants those which are compatible with an energized electrical or electronic component. In a fourth aspect, the present invention provides a lubricant which is compatible with an energized electrical or electronic component, selected using the method of the third aspect.

DETAILED DESCRIPTION OF THE INVENTION

Figure 1:
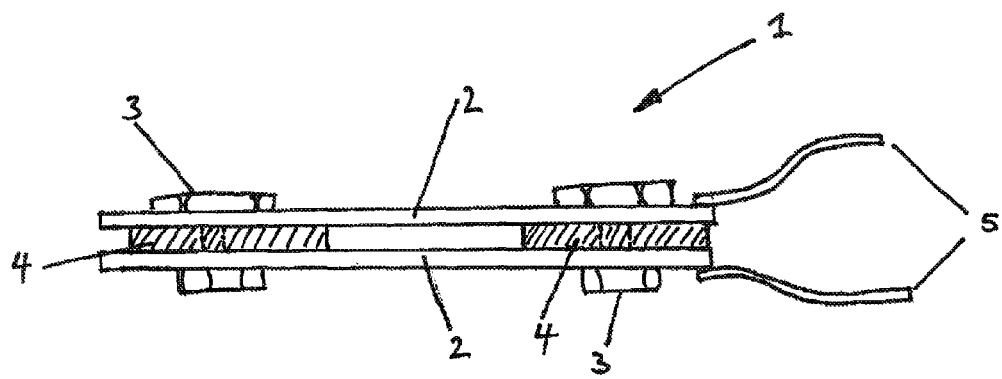
FIG. 1 shows an example of a test apparatus of the present invention

The test apparatus comprises at least one pair of conductors. The conductors may be fabricated from any electrically conducting materials but it is preferable that they are fabricated from materials which are representative of the conducting materials found in the electrical and electronic devices used in the control systems of mechanical equipment. Preferably, each conductor of the pair of conductors is a metal such as copper, silver, aluminum, gold or a metal substrate or alloy plated with a metal such as copper, silver, aluminum, gold. Each conductor of the pair of conductors may be fabricated from the same material or from different materials. Preferably, each conductor of the pair of conductors is fabricated from the same material.

The conductors are separated by an insulator. The insulator may be fabricated from any insulating material but it is preferably fabricated from a material which is representative of the insulating materials found in the electrical and electronic devices used in the control systems of mechanical equipment. Suitable materials are those used in the manufacture of electrical circuit-board substrates. Representative materials would be: nylon (polyaramide), Teflon (polyperfluoro olefins), Bakelite (polyphenols) and similar materials. It is critical that the insulator does not extend across the whole of the opposing surfaces of the conductors. This is because when the test apparatus is in use, the fluid should be able to penetrate between the conductors, so trapping small volumes of fluid in the path of electrical conduction. This is important as it mimics the environments experienced by real electrical and electronic devices and so allows an evaluation of the fluid which is representative of real-life operations.

The test apparatus can be of any suitable design. In one simple and preferred form, the test apparatus comprises two identical conducting strips of rectangular form arranged substantially congruently and separated by an insulator. The insulator comprises two regions of insulating material each conveniently situated towards the ends of, and interposed between, the conductors. In a preferred embodiment, the insulator comprises two annular spacers or washers which are interposed between the conducting strips and held in place via holes in the conductors using insulating fasteners such as plastic (e.g. nylon) machine bolts and nuts. In one embodiment, the spacers or washers are adapted so as to have channels or grooves on at least one face. In use, this allows the fluid to penetrate into the region of the fastener. Other designs may readily be conceived to achieve the same objective. For example, the conductors may be clamped together rather than bolted or the insulator may be in the form of a non-conducting resin or glue which is used to bond the conductors together. The conductors may also be of any shape and need not both be of the same size and shape.

Current may be supplied to the conductors by any suitable means. Conveniently, a wire is soldered or otherwise attached to each conductor. The choice of wire will be determined by factors such as the magnitude of the electrical current to be applied to the test apparatus and the temperature at which the testing will be conducted. Current may be applied by connecting the conductors to a source of electrical power such as a power supply or a battery. The voltage applied should be representative of the application being simulated. For vehicle applications that would normally be from 6 to 42 volts direct current. However, for hybrid transmission applications it may be from 6 to 400 volts or more, and may be either direct or alternating current. In one preferred embodiment, the current applied to the test apparatus is a direct current.

It is also within the scope of the present invention for the test apparatus to comprise a plurality of pairs of conductors. Where more than one pair of conductors is present, the pairs should be suitably electrically insulated from one another either by adequate physical separation or by making use of suitable insulating means. Where more than one pair of conductors is present, each pair may be identical in terms of their construction and materials of fabrication or they may be different.

The fluid is contained in a suitable vessel. No particular limit is placed on either the size or shape of the vessel although for reasons of economy, it may be desirable not to utilise more fluid than is necessary. The vessel must be of sufficient size such that the test apparatus can be contacted with the fluid. It is preferred that the test apparatus be completely submerged in the fluid although results may be obtained provided at least part of the test apparatus is in contact with the fluid.

The temperature at which testing is run is dependent on the type of fluid to be tested. Normally testing will be conducted at a temperature which is representative of the actual temperature which the fluid would experience when in use. Typically, for a manual transmission fluid or axle gear oil, this would be from about 60 to 100° C., for an automatic transmission fluid, CVT fluid or DCT fluid about 80 to 130° C., and for an engine oil about 80 to 160° C. Preferably, means are provided to heat or cool the lubricating fluid and/or to hold the fluid at a selected temperature. Suitable means may be to place the vessel containing the test apparatus and lubricating fluid into a thermostatically-controlled oil bath or heating block. Of course, temperatures less representative of actual working fluid temperature (either higher or lower) may also be used although adequate safety precautions should be taken if the chosen temperature approaches or exceeds the flash point of the test fluid.

If desired, other fluids, additives or chemical species may be added to the lubricating fluid to ascertain what effect these may have on compatibility. For example, water may be added to evaluate the effect of water contamination of the lubricant, or of humidity. Any water used may also contain ionic species such as those which have been observed to arise through contamination from external sources. Examples include sodium, potassium, calcium, magnesium ions, chloride, bromide and sulphate.

In preferred embodiments of all aspects, the lubricant is a lubricating oil. Suitable oils are derived from natural lubricating oils, synthetic lubricating oils, and mixtures thereof.

Natural lubricating oils include animal oils, vegetable oils (e.g., castor oil and lard oil), petroleum oils, mineral oils, and oils derived from coal or shale. The preferred natural lubricating oil is mineral oil.

Suitable mineral oils include all common mineral oil basestocks. This includes oils that are naphthenic or paraffinic in chemical structure. Oils that are refined by conventional methodology using acid, alkali, and clay or other agents such as aluminum chloride, or they may be extracted oils produced, for example, by solvent extraction with solvents such as phenol, sulfur dioxide, furfural, dichlordiethyl ether, etc. They may be hydrotreated or hydrofined, dewaxed by chilling or catalytic dewaxing processes, or hydrocracked. The mineral oil may be produced from natural crude sources or be composed of isomerized wax materials or residues of other refining processes.

Typically the mineral oils will have kinematic viscosities of from 2.0 $mm^2/s$ (cSt) to 10.0 $mm^2/s$ (cSt) at 100° C. The preferred mineral oils have kinematic viscosities of from 2 to 8 $mm^2/s$ (cSt), and most preferred are those mineral oils with viscosities of 3 to 6 $mm^2/s$ (cSt) at 100° C.

Synthetic lubricating oils include hydrocarbon oils and halo-substituted hydrocarbon oils such as oligomerized, polymerized, and interpolymerized olefins [e.g., polybutylenes, polypropylenes, propylene, isobutylene copolymers, chlorinated polylactenes, poly(1-hexenes), poly(1-octenes), poly-(1-decenes), etc., and mixtures thereof]; alkylbenzenes [e.g., dodecyl-benzenes, tetradecylbenzenes, dinonyl-benzenes, di(2-ethylhexyl)benzene, etc.]; polyphenyls [e.g., biphenyls, terphenyls, alkylated polyphenyls, etc.]; and alkylated diphenyl ethers, alkylated diphenyl sulfides, as well as their derivatives, analogs, and homologs thereof, and the like.

The preferred oils from this class of synthetic oils are Group IV basestocks, i.e. polyalphaolefins (PAO), including hydrogenated oligomers of an alpha-olefin, particularly oligomers of 1-decene, especially those produced by free radical processes, Ziegler catalysis, or cationic, Friedel-Crafts catalysis.

The polyalphaolefins typically have viscosities in the range of 2 to 20 cSt at 100° C., preferably 4 to 8 cSt at 100° C. They may, for example, be oligomers of branched or straight chain alpha-olefins having from 2 to 16 carbon atoms, specific examples being polypropenes, polyisobutenes, poly-1-butenes, poly-1-hexenes, poly-1-octenes and poly-1-decene. Included are homopolymers, interpolymers and mixtures.

Synthetic lubricating oils also include alkylene oxide polymers, interpolymers, copolymers, and derivatives thereof where the terminal hydroxyl groups have been modified by esterification, etherification, etc. This class of synthetic oils is exemplified by: polyoxyalkylene polymers prepared by polymerization of ethylene oxide or propylene oxide; the alkyl and aryl ethers of these polyoxyalkylene polymers (e.g., methyl-polyisopropylene glycol ether having an average molecular weight of 1000, diphenyl ether of polypropylene glycol having a molecular weight of 1000-1500); and mono- and poly-carboxylic esters thereof (e.g., the acetic acid esters, mixed $C_3$-$C_8$ fatty acid esters, and $C_{12}$ oxo acid diester of tetraethylene glycol).

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoethers, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebasic acid with two moles of tetraethylene glycol and two moles of 2-ethyl-hexanoic acid, and the like. A preferred type of oil from this class of synthetic oils is adipates of $C_4$ to $C_{12}$ alcohols.

Esters useful as synthetic lubricating oils also include those made from $C_5$ to $C_{12}$ monocarboxylic acids and polyols and polyol ethers such as neopentyl glycol, trimethylolpropane pentaerythritol, dipentaerythritol, tripentaerythritol, and the like.

The lubricating oils may be derived from refined, rerefined oils, or mixtures thereof. Unrefined oils are obtained directly from a natural source or synthetic source (e.g., coal, shale, or tar sands bitumen) without further purification or treatment. Examples of unrefined oils include a shale oil obtained directly from a retorting operation, petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Re-refined oils are obtained by treating used oils in processes similar to those used to obtain the refined oils. These re-refined oils are also known as reclaimed or reprocessed oils and are often additionally processed by techniques for removal of spent additives and oil breakdown products.

Another class of suitable lubricating oils are those basestocks produced from oligomerization of natural gas feed stocks or isomerization of waxes. These basestocks can be referred to in any number of ways but commonly they are known as Gas-to-Liquid (GTL) or Fischer-Tropsch base stocks.

In a preferred embodiment of all aspects of the present invention the lubricating oil is a transmission oil, preferably a manual transmission lubricant, an automatic transmission fluid (ATF) a continuously variable transmission fluid (CVTF) or a dual clutch transmission fluid (DCTF). As is known in the art, such fluids, in addition to a major proportion of a lubricating oil, will commonly contain chemical additive species. For the avoidance of doubt, it will be understood that reference to lubricating fluids in this specification embraces lubricating oils containing chemical additive species.

Suitable chemical additive species will be known to those skilled in the art and include dispersants, detergents, friction modifiers, anti-wear additives, anti-oxidants, corrosion inhibitors, anti-foaming additives, viscosity modifiers and seal-swell agents.

The invention will now be described by way of non-limiting example with reference to the attached drawings.

Figure 2:
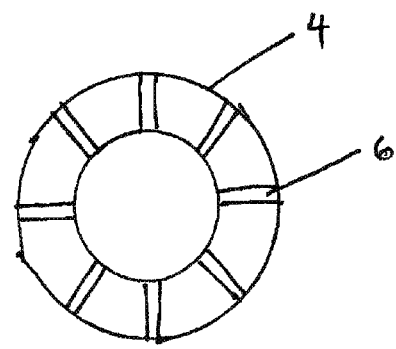
FIG. 2 shows an annular spacer suitable for use in a test apparatus
Figure 3:
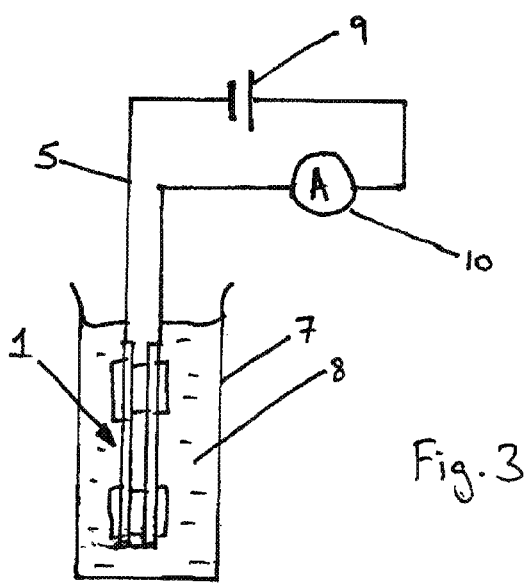
FIG. 3 shows a test apparatus in use

As shown in FIG. 1, a test apparatus (1) can comprise two copper conductors (2) separated by two nylon washers (4). The conductors are connected together using nylon nuts and bolts (3) through holes drilled in the conductors. Electrical leads (5) are soldered to each of the conductors. In one embodiment the washers (4) may be modified such as to have grooves (6). In use, the test apparatus is submerged in a test liquid (8) contained within a reservoir (7). If used, the grooves (6) permit the test fluid to penetrate into the regions of the test apparatus where the conductors and the insulators are in intimate contact. In FIG. 2, narrow, radial grooves are shown on one face of the washer (4). Of course, grooves of other sizes and shapes can be contemplated and these can be provided also on the other face of the washer. The electrical leads (5) are connected to a battery (9) and the current flowing through the test apparatus is monitored using an ammeter (10).

Figure 4:
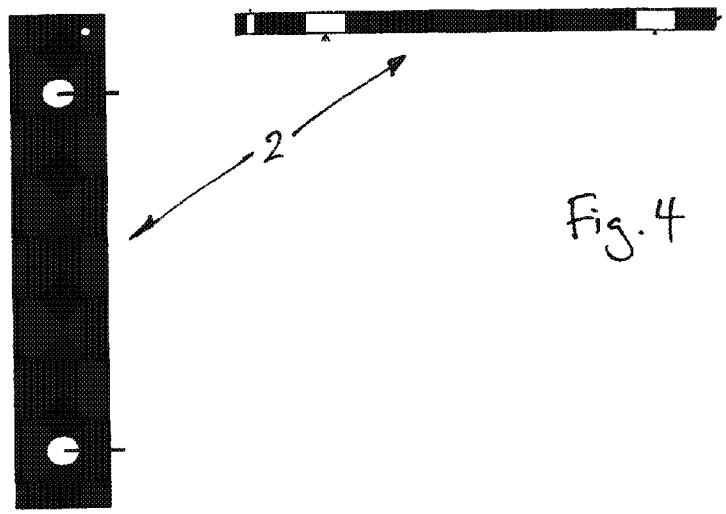
FIG. 4 shows an ASTM D-130 copper strip which is suitable as a conductor

In a worked example, two coppers strips of the type normally used to conduct ASTM D-130 copper corrosion testing were used as conductors (76.2 mm×12.7 mm×3.2 mm). These strips were machined as shown in FIG. 4 to accept the insulating fasteners and conducting wires. Prior to assembling the test apparatus the surfaces of the conductors were carefully cleaned as per ASTM D130-12 to remove any oxidation, coatings, chemical deposits, corrosion or finger prints. This was accomplished using 400 grit silicon carbide paper. Also suitable are mild abrasives such as steel wool, e.g. #0000 steel wool, or an abrasive compound such as pumice, rotten stone, silicon carbide or diamond polishing compounds. After abrasive cleaning, the conductors were thoroughly washed with a solvent (heptane) and allowed to dry. Gloves were used for subsequent handling so as not to re-contaminate the cleaned surfaces.

The conductors were separated from one another using 0.83 mm thick nylon washers, 12.7 mm in diameter with a 6.3 mm center hole, and fastened together using 10×24 nylon bolts and nuts. Each washer was grooved on both sides with an pattern with grooves which were approximately $\frac{1}{10}^{th}$ of the washer thickness. Once assembled, the test apparatus was placed into a test-tube, 25.4 mm diameter and 200 mm long, and the test fluid (approx. 25 ml) was added. The test-tube containing the test apparatus and the lubricating oil to be tested was then placed into a thermostatically-controlled oil bath and heated to 90° C.

Figure 5:
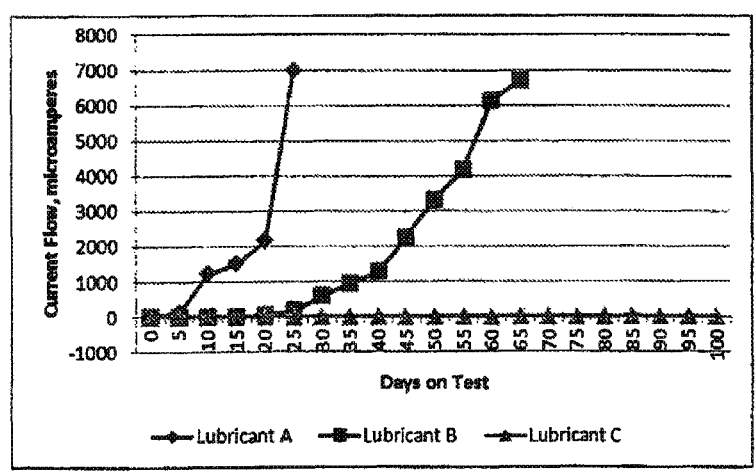
FIG. 5 is a graph showing the current flow measured over time for three different test fluids.

To conduct the tests, the conductors were connected to a dry-cell battery pack capable of supplying nominally 12 volts DC. Actual measured voltage was 12.9 volts. FIG. 5 is a plot of current flow over time. Three different fluids were tested. Two (Lubricant A and Lubricant B) were commercially available manual transmission lubricants and a third (Lubricant C) was an experimental lubricant designed for the same purpose. The table below gives the elemental analysis of the three fluids. Values given are in mass percent.

|  | Lubricant | | |
| Element | A | B | C |
| --- | --- | --- | --- |
| B | 0.013 | 0.012 | 0.010 |
| N | 0.100 | 0.100 | 0.180 |
| P | 0.038 | 0.064 | 0.037 |
| S | 0.710 | 1.020 | 0.060 |

In the test, a failure was deemed to have occurred by the failure of a 0.5 ampere fuse in the circuit. Measurement of the actual current flow in failing samples normally yielded values that exceeded 5 amperes.

Lubricant A was a lubricant with a known poor compatibility with metals. Lubricant B was lubricant with known better compatibility but which still had been observed to give rise to some field issues. Lubricant C was formulated to minimize the conduction of electrical current and the formation of conducting deposits. Examination of the tested parts from Lubricants A and B revealed heavy deposits of copper sulfide which had formed bridges between the two conducting copper strips. This caused a short circuit and hence the very high currents measured. Even though Lubricants A and C had broadly similar elemental sulfur contents, no excessive current flow was seen for Lubricant C throughout the 100 day duration of the test. Inspection of the test parts revealed no build-up of copper sulfide.

This testing shows that the method and device of the present invention are capable of quickly and simply discriminating between good and bad-performing lubricants from the perspective of protecting energized conductors from short-circuits due to build-up of electrically conductive chemical deposits or failure due to corrosion of the test electrodes.

What is claimed is:

1. A method of determining the compatibility of a lubricating fluid with an energized electrical or electronic component, the method comprising:
    (a) contacting a test apparatus with the fluid;
    (b) applying a direct electrical current to the test apparatus; and
    (c) monitoring the current flow through the test apparatus over time;
    wherein the test apparatus comprises at least one pair of conductors separated by an insulator; wherein the insulator does not extend across the whole of the opposing surfaces of the conductors;
    wherein the or each pair of conductors comprises two identical conducting strips of rectangular form arranged substantially congruently and separated by the insulator;
    wherein the insulator comprises two annular spacers or washers which are interposed between the conducting strips and held in place via holes in the conducting strips using insulating fasteners;
    wherein the spacers or washers are adapted so as to have channels or grooves on at least one face; and
    wherein the direct electrical current is applied across the or each pair of conductors.

2. The method according to claim 1 wherein the test apparatus is submerged in the fluid.

3. The method according to claim 1 wherein the fluid is a lubricating oil.

4. The method according to claim 1 wherein a heating and/or cooling device is provided to heat or cool the fluid and/or to hold the fluid at a selected temperature.

5. The method according to claim 1 wherein each conductor of the pair of conductors is a metal or a metal substrate or alloy plated with a metal.

6. The method according to claim 5 wherein the metal is at least one metal selected from copper, silver, aluminum, and gold.

7. The method according to claim 1 wherein the insulator is a material useful in the manufacture of electrical circuit-board substrates.

8. The method according to claim 7 wherein the insulator is at least one material selected from nylon, Teflon® and Bakelite®.

9. The method according to claim 1 wherein the or each pair of conductors are separated by between 0.1 and 10.0 mm.

10. The method according to claim 9 wherein the or each pair of conductors are separated by between 0.5 and 5 mm.

11. A device for determining the compatibility of a lubricating fluid with an energized electrical component, the device comprising a fluid reservoir and a test apparatus having at least one pair of conductors separated by an insulator,
    wherein the insulator does not extend across the whole of the opposing surfaces of the conductors;
    wherein the or each pair of conductors comprises two identical strips of rectangular form arranged substantially congruently and separated by the insulator;
    wherein the insulator comprises two annular spacers or washers which are interposed between the conducting strips and held in place via holes in the conducting strips using insulating fasteners;
    wherein the spacers or washers are adapted so as to have channels or grooves on at least one face; a current source adapted to apply a direct electrical current across the or each pair of conductors; and a monitoring device for monitoring the current flow through the test apparatus over time; and
    wherein the test apparatus is configured such that in use, the conductors are in contact with the fluid.

* * * * *